(12) United States Patent
Buck et al.

(10) Patent No.: US 6,306,665 B1
(45) Date of Patent: Oct. 23, 2001

(54) COVALENT BONDING OF MOLECULES TO AN ACTIVATED SOLID PHASE MATERIAL

(75) Inventors: Robert Lee Buck, Sherwood; Huiying Wang, Portland; Timothy Patrick Hyatt, Dundee; Paul Andrew Mueggler, Portland, all of OR (US)

(73) Assignee: A-Fem Medical Corporation, Portland, OR (US)

( * ) Notice: Subject to any disclaimer, the term of this patent is extended or adjusted under 35 U.S.C. 154(b) by 0 days.

(21) Appl. No.: 09/417,957

(22) Filed: Oct. 13, 1999

(51) Int. Cl.$^7$ .................................................. G01N 33/544
(52) U.S. Cl. .................. 436/530; 436/518; 436/524; 436/527; 436/528; 436/529; 436/530; 436/532; 436/535; 436/538; 436/541; 436/162; 436/166; 436/168; 436/169; 436/170; 435/4; 435/6; 435/7.1; 435/7.5; 435/7.92; 435/286.5; 435/287.2; 435/287.3; 435/287.7; 435/287.8; 435/287.9; 422/55; 422/56; 422/58; 422/60; 422/62; 422/68.1
(58) Field of Search .................................. 422/55, 56, 57, 422/58, 60, 61, 62, 68.1, 69; 435/4, 6, 7.1, 7.5, 7.92, 128, 130, 286.5, 287.2, 287.3, 287.7, 287.8, 287.9; 436/518, 524, 527, 528, 529, 530, 532, 535, 538, 541, 162, 166, 168, 169, 170, 808; 559/419, 421

(56) References Cited

U.S. PATENT DOCUMENTS

| | | |
|---|---|---|
| 3,519,538 | 7/1970 | Messing et al. . |
| 3,857,931 | 12/1974 | Hager . |
| 4,045,384 | 8/1977 | Dorman . |
| 4,102,746 | 7/1978 | Goldberg . |
| 4,168,146 | 9/1979 | Grubb et al. . |
| 4,169,014 | 9/1979 | Goldberg . |
| 4,313,734 | 2/1982 | Leuvering . |
| 4,366,241 | 12/1982 | Tom et al. . |
| 4,425,438 | 1/1984 | Bauman et al. . |
| 4,703,017 | 10/1987 | Campbell et al. . |
| 4,806,312 | 2/1989 | Greenquist . |
| 4,824,870 | 4/1989 | Pemawansa et al. . |
| 4,851,356 | 7/1989 | Canfield et al. . |
| 4,861,711 | 8/1989 | Friesen et al. . |
| 4,886,836 | 12/1989 | Gsell et al. . |
| 4,916,056 | 4/1990 | Brown, III et al. . |
| 4,943,522 | 7/1990 | Eisinger et al. . |
| 4,956,275 | 9/1990 | Zuk et al. . |
| 4,959,305 | 9/1990 | Woodrum . |
| 4,961,852 | 10/1990 | Pemawansa et al. . |
| 4,963,468 | 10/1990 | Olson . |
| 4,981,786 | 1/1991 | Dafforn et al. . |
| 4,992,172 | 2/1991 | Pemawansa et al. . |
| 4,999,285 | 3/1991 | Stiso . |
| 5,002,883 | 3/1991 | Bieniarz et al. . |
| 5,008,080 | 4/1991 | Brown, III et al. . |
| 5,063,109 | 11/1991 | Bieniarz et al. . |
| 5,073,484 | 12/1991 | Swanson et al. . |
| 5,075,078 | 12/1991 | Osikowicz et al. . |
| 5,114,673 | 5/1992 | Berger et al. . |
| 5,120,643 | 6/1992 | Ching et al. . |
| 5,160,626 | 11/1992 | Pemawansa et al. . |
| 5,229,073 | 7/1993 | Luo et al. . |
| 5,266,497 | 11/1993 | Imai et al. . |
| 5,416,000 | 5/1995 | Allen et al. . |
| 5,451,504 | 9/1995 | Fitzpatrick et al. . |
| 5,591,645 | 1/1997 | Rosenstein . |
| 5,622,871 | 4/1997 | May et al. . |
| 5,654,162 | 8/1997 | Guire et al. . |
| 5,656,503 | 8/1997 | May et al. . |

FOREIGN PATENT DOCUMENTS

| | | |
|---|---|---|
| 0362809 | 4/1990 | (EP) . |
| WO 89/05978 | 6/1989 | (WO) . |

OTHER PUBLICATIONS

Lindner et al., Tartaric acid derivatives as chiral sources for enantioseparation in liquid chromatography, J. Pharm. Biomed. Anal. 2(2): 183–189 (1984). Abstract Only.*

Lou, S.C. et al., "One–Step Competitive Immunochromatographic Assay for Semiquantitative Determination of Lipoprotein(a) in Plasma, " Clin. Chem., 39(4):619–624 (1993).

Canas, B. et al., "Covalent Attachment of Peptides to Membranes for Dot–Blot Analysis of Glycosylation Sites and Epitopes," Analytical Biochemistry, 211, 179–182 (1993).

Lauritzen, E. et al., "Dot Immunobinding and Immunoblotting of Picogram and Nanogram Quantities of Small Peptides on Activated Nitrocellulose," Journal of Immunological Methods, 131, 257–267 (1990).

(List continued on next page.)

Primary Examiner—Long V. Le
Assistant Examiner—Gailene R. Gabel
(74) Attorney, Agent, or Firm—Klarquist Sparkman, LLP

(57) ABSTRACT

Microporous solid phase materials that are suitable for lateral flow and other assays for detecting the presence of analytes in test samples, that are stable under variations in humidity and, even after storage for extended periods of time, can form stable covalent bonds with molecules containing a free primary or secondary amine group or sulfhydryl group are described. The invention further concerns chemically derivatized solid phase materials, and conjugates comprising such materials. Examples of lateral flow devices for the quantitative or semi-quantitative determination of an analyte in a biological sample are described.

16 Claims, 4 Drawing Sheets

OTHER PUBLICATIONS

Lauritzen, E. et al., "Peptide Dot Immunoassay and Immunoblotting: Electroblotting from Aluminum Thin–Layer Chromatography Plates and Isoelectric Focusing Gels to Activated Nitrocellulose," Electrophoresis, 14, 852–859 (1993).

Marlow, S.J. et al., "Immuno Slot–Blot Assay Using a Membrane Which Covalently Binds Protein," Journal of Immunological Methods, 101, 133–139 (1987).

Másson, M. et al., "Chemical Activation of Nitrocellulose Membranes for Peptide Antigen–Antibody Binding Studies: Direct Substitution of the Nitrate Group and Diaminoalkane," Electrophoresis, 14, 860–865 (1993).

Pemawansa, K.P.W. et al., "An Advanced Affinity Membrane for Covalent Binding of Amino Ligands," BioTechniques, vol. 9, No. 3 (1990).

Weetall, H.H. et al., "Porous Glass for Affinity Chromatography Applications," Methods Enzymol, 34(): 59–72 (1974).

* cited by examiner

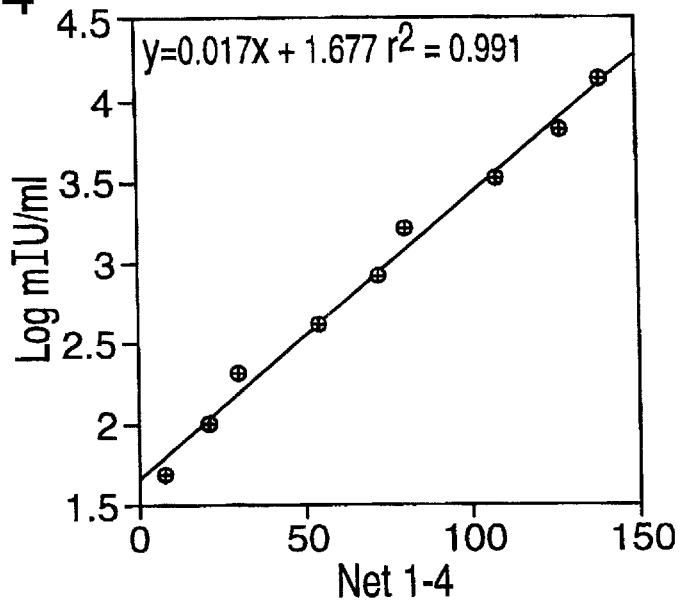
FIG. 4 DIRECT LINEAR FIT USING RANGE OF 50 MIU/ML TO 12.8 IU/ML HCG
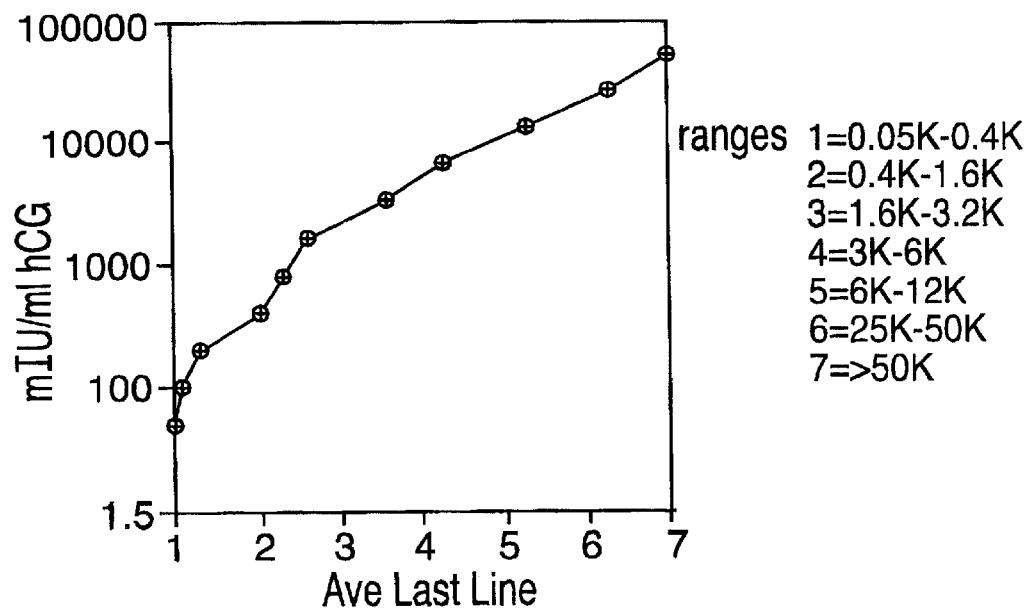
FIG. 5 SEMI-QUANTITATIVE DETERMINATION OF LAST VISIBLE LINE ON RAPIDSENSE STRIP

COVALENT BONDING OF MOLECULES TO AN ACTIVATED SOLID PHASE MATERIAL

FIELD

The present invention concerns the immobilization of molecules on a solid phase material, more specifically a derivatized solid phase material and covalent bonding of molecules to that derivatized solid phase material, and devices made using the material.

BACKGROUND

The last two decades have seen an increase in the availability of drugs for the treatment of a variety of diseases, the identification of a wide variety of compounds associated with pathogens, and the need to detect small amounts of contaminants in the environment and industrial effluents. Thus, assays are needed and used for detecting the presence of analytes in test samples in fields such as clinical and forensic medicine, environmental testing, food quality assurance, and drug use testing and related areas.

A variety of diagnostic tests have been developed for the routine identification or monitoring of physiological and pathological conditions (e.g., pregnancy, cancer, endocrine disorders, infectious diseases) using a variety of biological samples (e.g., urine, serum, plasma, blood, saliva) and environmental samples (e.g., natural fluids and plant effluents). Many of these diagnostic tests are based on the highly specific interactions between specific binding pairs. Examples of such binding pairs include antigen/antibody, hapten/antibody, lectin/carbohydrate, apoprotein/cofactor and biotin/streptavidin. Furthermore, many of these tests involve devices (e.g., lateral-flow test strips, flow-through tests) with one or more of the members of a binding pair attached to a mobile or immobile solid phase material such as latex beads, glass fibers, glass beads, cellulose strips or nitrocellulose membranes. The attachment of molecules such as antibodies, antigens, biotin or streptavidin to a solid phase material normally involves either passive adsorption or covalent bonding.

Current methodology for the attachment of molecules (e.g., peptides and proteins) to microporous solid phase material (e.g., nitrocellulose in lateral-flow and flow-through devices) often involves the passive adsorption of molecules to the solid phase material. The interaction between the attached molecules and solid phase material is primarily hydrophobic in nature, based on van der Waals forces, or due to hydrogen bonding. Passive adsorption is subject to several limitations. To consistently maintain their protein-interactive properties, solid phase materials like nitrocellulose membranes must remain hydrated and be stored in a stable environment of controlled humidity and temperature. Furthermore, passive adsorption is not effective in immobilizing small molecules (≦1000 Daltons) such as drugs, hormones and small peptides (see Lauritzen et. al., *J. Immunol. Methods*, 131(2):257–267 (1990)) or nucleic acid polymers in conformations that are conducive to nucleic acid hybridization and palindromic sequence folding. Due to these passive adsorption limitations, small molecules (<1000 Daltons), nucleic acid polymers and some proteins preferably are covalently bound to a solid phase material to increase stability and prevent palindromic sequence folding.

It is also preferable to bond the molecule to a microporous solid phase material that has flow properties suitable for lateral-flow applications.

U.S. Pat. No. 3,857,931 shows that peptides and proteins can be chemically bonded to latex particles that have surface carboxyl groups. Carbodiimide can be reacted directly with the carboxyl groups on the latex to form a transient activated intermediate acyl-isourea, which in turn reacts with amino groups on a molecule to form a stable amide bond. This amide bond couples the peptide or protein to the latex particles' surface. A disadvantage of this process is the inability to control the undesirable and indiscriminate reaction of carbodiimide with the carbonyl groups that are also present on proteinic molecules. Thus, carbodiimide-activated carboxyls on a protein may react with amino groups on the protein to cause intra- or inter-protein crosslinking. Crosslinking occurs especially when the protein or peptide contains relatively large amounts of aspartic and glutamic acid, since those amino acids contain free carboxyl groups. Crosslinking can result in conformational or structural distortion of the proteinic molecule that in turn can affect assay sensitivity.

U.S. Pat. No. 4,045,384 states that carboxylated latex can be reacted with a water-soluble carbodiimide and water-solubilized N-hydroxy compound, such as N-hydroxybenzotriazole, to form an active ester latex. This activated ester latex can be reacted with the amino groups of a protein to covalently bond the protein to latex particles via amide bonds in a three-step process that eliminates protein crosslinking side reactions. This process, however, is not suitable for lateral-flow applications.

Amine-bearing solid phase materials can be chemically derivatized with extended-length, heterobifunctional crosslinking reagents to form an activated solid phase material that will form a covalent bond with thiol-bearing peptides or proteins. See Bieniarz et al., U.S. Pat. Nos. 5,002,883 and 5,063,109. Such solid phase materials include those polymers, glasses, and natural products that contain primary, secondary or tertiary amine groups. Also, solid phase materials containing nitrile groups may be reduced to yield amine groups to produce amine-bearing solid phase materials. Amine-bearing solid phase materials, however, are not suitable for lateral-flow applications.

Activated microporous membranes are commercially available for the covalent bonding of molecules that contain amino groups. For example, the UltraBind™ membrane (Pall Gelnan Laboratory, Ann Arbor, Mich.) is a polysulfone/polyacrolein-type membrane that has a high concentration of aldehyde active sites available for covalent bond formation with molecules that contain amino groups. See Pemawansa et al., *BioTechniques* 9(3):352–355 (1990) and Pemawansa et al., U.S. Pat. Nos. 4,824,870, 4,961,852, 5,160,626. Also activated nylon (Biodyne™, and Immunodyne™, Pall Corporation, Glen Cove, N.Y.) and activated polyvinylidene difluoride (Irnmobilon™, Millipore, Bedford, Mass.) also are available for the covalent attachment of proteins as discussed in Gsell et al., U.S. Pat. No . 4,886,836; Marlow et al., *J. Immuno, Methods* 30 101:133–139 (1987); and Canas et al., *Analytical Biochemistry* 211:179–182 (1993). Although the membranes identified above are well suited for blotting applications, those membranes have poor flow characteristics and minimal utility for lateral flow applications. Nitrocellulose membranes are generally better suited to lateral flow applications, and many commercially available pore sizes are available. However, in an untreated state, fluid-permeable, microporous solid phase materials, such as nitrocellulose or glass fibers, lack the organic functionality necessary to effect covalent bonding to molecules containing amino groups.

Methods for the covalent bonding of peptides and proteins to activated nitrocellulose have been reported in the scientific literature. For example, a method to covalently bond peptides and proteins through a diaminoalkane spacer to nitrocellulose was developed for immunochemical applications. See Masson et al., *Electrophoresis* 14(9):860–865 (1993). Also, divinylsulfone, a spacer of ethylenediamine, and glutaraldehyde have been used to produce an activated nitrocellulose. Peptides were attached to this activated nitrocellulose by reaction of the amino group with the free aldehyde groups, forming unreduced Schiff-base bonds. See Lauritzen et al. in the *J. Immunol, Methods* 131(2):257–267 (1990) and *Electrophoresis* 14(9):852–859 (1993).

SUMMARY

An object of the present invention is to develop microporous solid phase materials that are suitable for lateral flow and other assays for detecting the presence of analytes in test samples, stable under variations in humidity and, even after storage for extended periods of time, can form stable covalent bonds with molecules containing a free primary or secondary amine group or sulfhydryl group. The invention involves chemically derivatized solid phase materials having Formula 1.

Formula 1

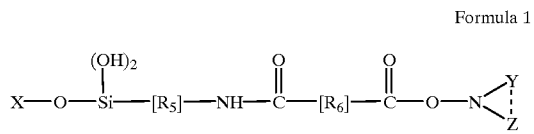

With reference to Formula 1, X is a hydroxyl-bearing solid phase material (e.g., nitrocellulose, cellulose, glass fibers and porous glass beads) $R_5$ is $(CH_2)_n(NH(CH_2)_m)_p$, wherein n is from 2 to 8, is from 2 to 8 and p is from 0 to 3. $R_6$ is selected from the group consisting of alkyl, cyclic alkyl, aromatic or heterocyclic groups containing 0 to 8 hydroxyl, hydroxycarbonyl or aminocarbonyl groups. $R_6$ may be derived from a crosslinking agent such as succinic anhydride, glutaric anhydride, ethylene glycol bis-(succinimidyl succinate), or ethylene glycol bis-(sulfosuccinicimidyl succinate). Y and Z are independently hydrogen, alkyl alkyl carbonyl, aromatic carbonyl or heterocyclic carbonyl groups, or N, Y and Z together are

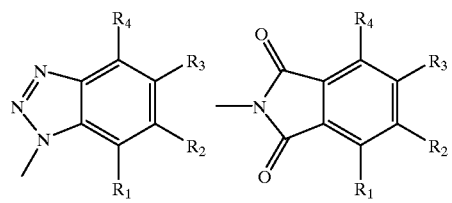

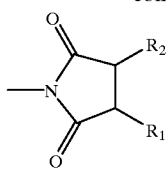

where $R_1$, $R_2$, $R_3$, and $R_4$ are selected from a group consisting of hydrogen, alkyl, carboxyl, sulfonate, aromatic or heterocyclic groups.

Alternatively, the invention also involves chemically derivatized solid phase materials having Formula 2.

Formula 2

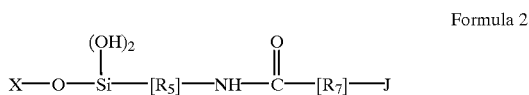

With reference to Formula 2, X and $R_5$ are as defined previously for Formula 1. $R_7$ is selected from the group consisting of alkyl, cyclic alkyl, aromatic or heterocyclic groups containing 0 to 8 hydroxyl, hydroxycarbonyl or aminocarbonyl groups. $R_7$ may vary depending on which bifunctional crosslinking reagent is used. J is selected from a group consisting of:

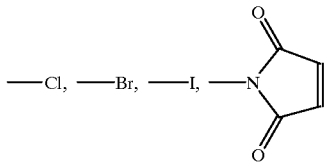

Examples of bifunctional crosslinking reagents that can produce structures of the type represented in Formula 2 include succinimidyl 6-maleimidylhexanoate; succinimidyl 6-(6-(((iodoacetyl)amino)hexanoyl)amino)hexanoate; succinimidyl 6-((iodoacetyl)amino)hexanoate; succinimidyl 4-(N-maleimidomethyl)cyclohexane-1-carboxylate; N-γ-maleimidobutyryloxy-succinimide ester; and N-γ-maleimidobutyryloxy-sulfosuccinimide ester.

The invention also involves a conjugate having Formula 3

Formula 3

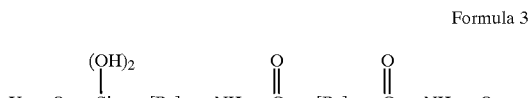

With reference to Formula 3, X, $R_5$ and $R_6$ are as defined previously for Formula 1. Q is any molecule that contains a free primary or secondary amine group, or that intrinsically contains any molecule to which a free primary or secondary amine group has been covalently attached.

The invention also involves a conjugate having Formula 4.

Formula 4

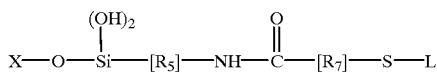

With reference to Formula 4, X, $R_5$ and $R_7$ are as defined previously for Formula 2. L is any molecule that contains a free sulfhydryl group or that intrinsically contains any molecule to which a free sulfhydryl group has been covalently attached.

The present invention also provides devices that include conjugates having Formulas 3 and/or 4. A more particular example of such a device was designed for the quantitative or semi-quantitative determination of an analyte in a biological sample using a lateral flow device, where the analyte contains two binding domains, an α-domain that is linked to an immobilized binding ligand and a β-domain that is linked to an indicator binding ligand. The device comprised a pad containing an indicator binding ligand and a contrast binding ligand. The indicator binding ligand comprised an indicator signal generator that has visual, spectrophotometric, colorimetric or fluorometric properties. The indicator binding ligand had immobilized on its surface a binding ligand specific for the β-domain of the analyte. The contrast binding ligand comprised a contrast signal generator having visual, spectrophotometric, colorimetic or fluorometric properties that contrast in different regions of the spectrum form the indicator binding ligand. The contrast binding ligand had immobilized on its surface a molecular domain that specifically binds to the immobilized binding ligand. The device also included a porous membrane in liquid transfer contact with the pad and the sample, whereby the indicator binding ligand and contrast binding ligand diffuse through the porous membrane by capillary action. The device also included an analyte test zone on the porous membrane. The analyte test zone contained a fixed limited number of immobilized α-domain-specific bind sites, where the limited number of immobilized α-domain-specific bind sites were immobilized on the porous membrane by reaction with a conjugate having Formulas 3 and/or 4

These and other aspects of the present invention will become evident upon reference to the detailed description.

BRIEF DESCRIPTION OF THE DRAWINGS

FIG. 4 is a graphical representation of a linear least squares fit of the average color intensity of the sum of lines 1–4 as measured on a Minolta CR-241 color analyzer of the multiple test line format (depicted in FIG. 2) for increasing concentrations of human chorionic gonadotropin(hCG).

FIG. 5 is a graphical representation of the average last line seen visually in the multiple line format (depicted in FIG. 2) for increasing concentrations of hCG.

DETAILED DESCRIPTION

I. Solid Phase Materials

Figure 1:
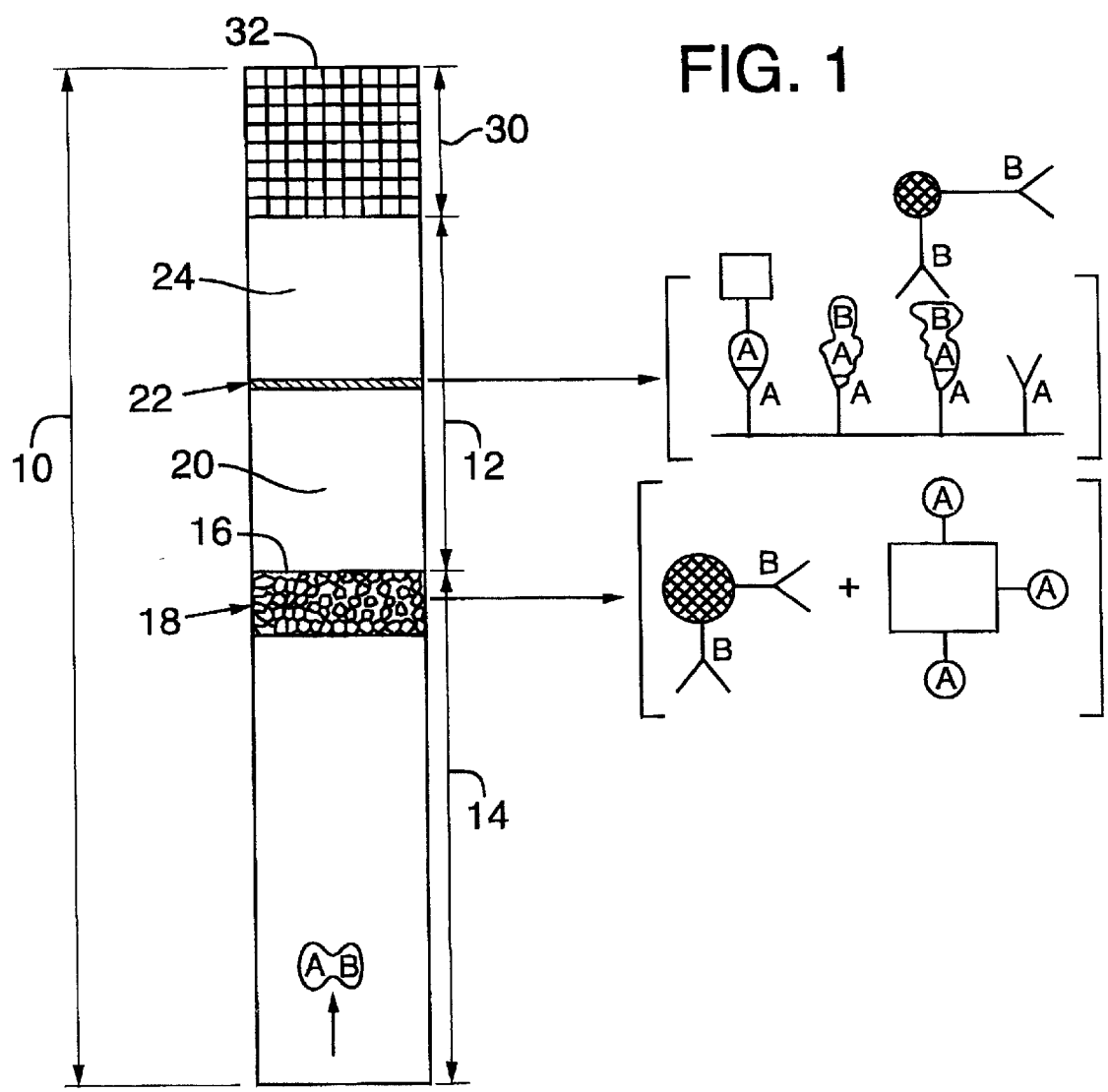
FIG. 1 is a schematic representation of a sandwich format LFD with a single test line that is compatible with semi-quantitative detection of large molecule analytes.

The present invention concerns derivatized solid phase materials having novel linking groups that can be used to covalently bond to the solid phase material any molecule that contains a free primary or secondary amine group or sulfhydryl group or to any molecule to which an amine group or sulfhydryl group has been covalently attached. The solid phase material can be any hydroxyl-containing solid phase material, including nitrocellulose, cellulose and glass, that is suitable for assays for detecting the presence of analytes in test samples. The present invention also concerns devices having such materials.

While the Examples that follow generally deal with microporous solid phase materials in the form of membranes, strips and pads, other solid phase configurations are possible, including but not limited to, fibers, beads, spheres and the like. For example, where the hydroxyl-containing solid phase material is available in fibrous, sphere or bead form, the fibers, spheres or beads can be derivatized as described in Examples 1, 2 and 3 and proteins such as antibodies can be conjugated to the derivatized solid phase material. The conjugated material can then be sewn, woven or otherwise attached or incorporated into a solid support such as cloth, a mat or woven or non-woven filter media. Also, as illustrated in Examples 6 and 7, the solid phase material may be laminated onto polyvinyl chloride ("PVC") or similar solid support.

A. Definitions

"Aminosilane" as used in the context of the present invention refers to an organosilane, gamma-aminopropyltriethoxysilane ($H_2NCH_2CH_2CH_2Si(OCH_2CH_3)_3$). Examples of other organosilanes or bridging agents that may be used in place of aminosilane include gamma-aminopropyltrimethoxysilane ($H_2NCH_2CH_2CH_2Si(OCH_3)_3$); N-beta(aminoethyl)-gamma-aminopropyltrimethoxysilane ($H_2NCH_2CH_2NHCH_2CH_2CH_2Si(OCH_3)_3$); and triamino-functional silane ($H_2NCH_2CH_2NHCH_2CH_2NHCH_2CH_2CH_2Si(OCH_3)_3$). As reported in the literature (U.S. Pat. Nos. 3,519,538, 4,102, 746, and 4,169,014) organosilane bridging agents can be used to bond or attach proteins, generally enzymes, to siliceous materials like porous glass or ceramic beads. Also, the attachment of the above-listed organofunctional silanes to nitrocellulose was reported by Union Carbide, *Union Carbide® Organofunctional Silanes Product and Applications*, in Specialty Chemicals: OrganoSilicon Product Information (1993).

"Bifunctional crosslinking reagent" means a reagent containing two reactive groups, the reagent thereby having the ability to covalently link two target groups. The reactive groups in a crosslinking reagent typically belong to the classes of functional groups including succinimidyl esters, maleimides and haloacetamides such as iodoacetamides.

Homobifunctional crosslinking reagents have identical reactive groups and are predominantly used to link like target groups such as two thiols or two amines.

Heterobifunctional crosslinking reagents include reactive groups having dissimilar chemistry, thereby allowing the formation of crosslinks between unlike functional groups.

"DICD" as used in the context of this specification means N,N-diisopropyl carbodiimide.

"DMF" means dimethylformamide.

"EDAC" means 1-ethyl-3-(3-dimethylaminopropyl) carbodiimide, $(CH_3)_2-N-CH_2-CH_2-CH_2-N=C=N-CH_2-CH_3$.

"HBT" refers to 1-hydroxybenzotriazole, shown below,

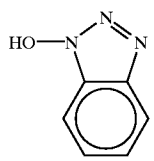

1- hydroxybenzotriazole which also is known as N-hydroxybenzotriazole.

"Leaving group" refers to a molecule (e.g., N-hydroxybenzotriazole, substituted derivatives of N-hydroxybenzotriazole, N,N-dialkylhydroxylamine, 1-hydroxypiperidine, N-hydroxysuccinimide and N-hydroxyphthalimide) that is displaced from a chemical bond by a displacing molecule (e.g. the α- or ε-amino group on an antibody) to form a new chemical bond that is more stable.

"Water-soluble carbodiimide" refers to those molecules having the formula

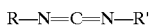

Water-Soluble Carbodiimide

Having a solubility of greater than 1 mg/ml in water and wherein R and R' can be the same or different and are selected from the group consisting of cycloalkyl groups having from 5 to 6 carbon atoms in the ring; alkyl groups of from 2 to 12 carbon atoms (e.g. ethyl, n-propyl, isopropyl, n-butyl, sec-butyl, isobutyl, tert-butyl, amyl, hexyl, heptyl, octyl, nonyl, decyl, undecyl, and dodecyl); monoarylsubstituted lower alkyl radicals (e.g. benzyl, α- and β-phenylethyl); monoaryl radicals (e.g. phenyl, morpholino, piperidyl); morpholinyl substituted lower alkyl radicals (e.g. ethyl morpholinyl); piperidyl substituted lower alkyl radicals (e.g. ethyl piperidyl); di-lower alkylamino; lower alkyl radicals; piperidyl substituted lower alkyl radicals (e.g. α, β and λ methyl or ethyl pyridyl); acid addition salts; and quaternary amines.

B. Discussion

One embodiment of the method of the present invention involves imparting an aliphatic amine functionality to a fluid-permeable, microporous solid phase material by covalently bonding an intermediate organosilane bridging or coupling agent directly to the solid phase material. Examples of useful organosilanes include, without limitation, aminosilane, gamma-aminopropyltrimethoxysilane $(H_2NCH_2CH_2CH_2Si(OCH_3)_3)$, N-beta(aminoethyl)-gamma-aminopropyltrimethoxysilane $(H_2NCH_2CH_2NHCH_2CH_2CH_2Si(OCH_3)_3)$, and triamino-functional silane $(H_2NCH_2CH_2NHCH_2CH_2NHCH_2CH_2CH_2Si(OCH_3)_3)$. Imparting an aliphatic amine functionality can be done by placing the solid phase material in a solution comprising from about 5% to about 15% organosilane at a pH of from about 3.0 to about 3.5 in water at room temperature (20 to 30° C.) for a period sufficient to form a bond, such as from about 2 to about 4 hours. The solid phase material is then removed from the organosilane solution and washed twice with, for example, 10 mM sodium phosphate buffer at (pH 8.0–9.0) containing 0.01% polyoxyethylenesorbitan monolaurate (Tween 20, Sigma Chemical, St. Louis, Mo.).

A variety of chemistries can be applied to the aliphatic amino group of the aminosilane bridge to covalently bond molecules containing either sulfhydryl groups or free primary or secondary amine groups to the chemically derivatized solid phase material. For example, the aliphatic amino group at the solid phase surface can be acylated (such as with succinic anhydride, glutaric anhydride or derivatives of both in a carbonate or phosphate buffer at pH 8.0 to 10.0) to produce an aliphatic carboxyl group on the surface of the solid phase material. The aliphatic carboxyl group thus formed can be washed with deionized water or additional buffer to remove any unreacted material and by-products and dried. The aliphatic carboxyl group at the surface of solid phase material can be coupled to an N-hydroxy compound (e.g., N-hydroxybenzotriazole, substituted derivatives of N-hydroxybenzotriazole, N,N-dialkylhydroxylamine, 1-hydroxypiperidine, N-hydroxysuccinimide and N-hydroxyphthalimide). This coupling can be done, for example, in the presence of a water-soluble carbodiimide at temperatures generally below room temperature, generally from about 2 to 5° C. for a period of time sufficient to achieve the coupling, such as from about 2 to about 4 hours, thereby forming a reactive ester. The reactive ester formed can be washed with 0.05% Tween 20 and dried to form a chemically derivatized fluid-permeable microporous solid phase material within the definition of Formula 1 as illustrated by the scheme shown immediately below for succinic anhydride and HBT.

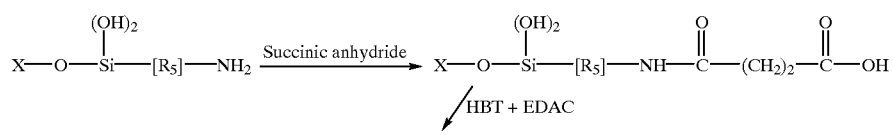

-continued

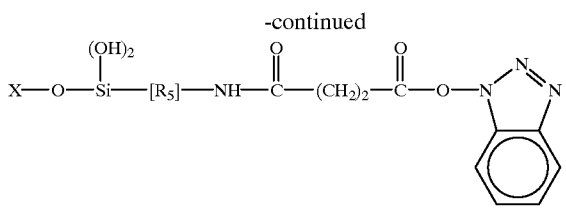

An alternative method for preparing the chemically derivatized solid phase materials of Formula 1 involves reacting the aliphatic anion group of the aminosilane bridge on the surface of the solid phase material with homobifunctional crosslinking reagents containing two amine reactive groups (e.g. succinyl di-N-hydroxybenzotriazole, ethylene glycol bis-(succinimidyl succinate), ethylene glycol bis-(sulfosuccinimidyl succinate), disuccinimidyl tartarate, disulfosuccinimidyl tartarate, disuccinimidyl glutarate, disuccinimidyl suberate). For example, succinyl di-N-hydroxybenzotriazole may be prepared by reacting succinic acid with HBT in the presence of DMF and a water-soluble carbodiimide, such as DICD, at 2 to 5° C. for 2 to 4 hours. A white, insoluble urea by-product, (CH3)2—CH—NH—C(O)—NH—CH—(CH3)2, produced during the reaction, can be separated from the succinyl di-N-hydroxybenzotriazole by centrifuging the mixture and decanting the supernate. Then the decanted succinyl di-N-hydroxybenzotriazole in DMF can be buffered to pH 8.0 to 10.0 with an aqueous buffer and reacted with the aliphatic amino group at the solid phase surface at 20 to 30° C. for 1 to 2 hours. The solid phase material is then removed from the solution, washed with deionized water and Tween 20 and dried to produce the following chemically derivatized fluid-permeable microporous phase material within the definition of Formula 1 as illustrated in the scheme provided immediately below.

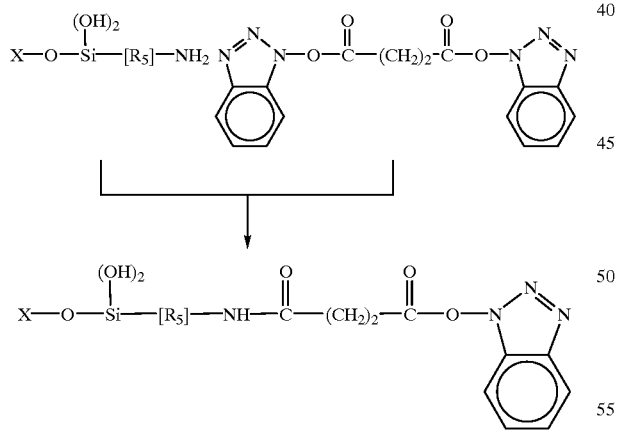

The derivatized solid phase material of Formula 1 is sufficiently stable to allow washing with aqueous solutions for sufficient periods to remove any remaining reactants. To avoid undesirable side reactions, molecules of interest should be bonded to the derivatized solid phase material preferably after the derivatized solid phase material of Formula 1 has been washed. Following washing and drying, the derivatized solid phase material of Formula 1 is stable for six to twelve months when stored with a desiccant.

Derivatized solid phase materials having Formula 2 can be prepared by reacting the aliphatic amino group of the aminosilane bridge with a heterobifunctional crosslinking reagent containing one amine reactive and one sulfhydryl reactive group [e.g. succinimidyl 6-maleimidylhexanoate; succinimidyl 6-(6-(((iodoacetyl)amino)hexanoyl)amino) hexanoate; succinimidyl 6-((iodoacetyl)amino)hexanoate; succinimidyl 4-(N-maleimidomethyl) cyclohexane-1-carboxylate; N-γ-maleimidobutyryloxy-succinimide ester; and N-γ-maleimidobutyryloxy-sulfosuccinimide ester]. For example, a chemically derivatized solid phase material of Formula 2 can be prepared by reacting the aliphatic amino groups of the aminosilane bridge on the surface of the solid phase material with succinimidyl 6-maleimidylhexanoate at pH 8.0–10.3 for 2–4 hours at 20–30° C. The solid phase material can then be removed from the solution, washed with deionized water and Tween 20 and dried to produce the following chemically derivatized fluid-permeable microporous phase material within the definition of Formula 2 as illustrated by the chemical scheme shown immediately below.

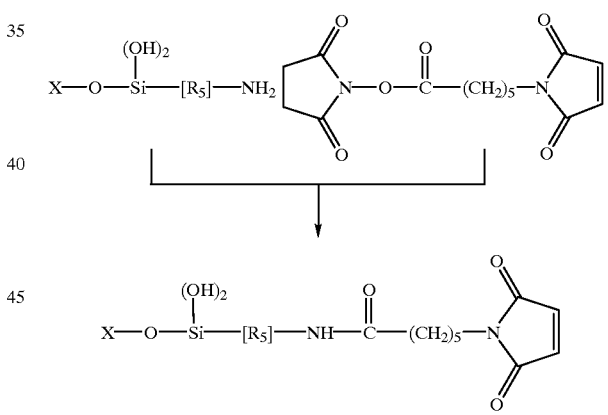

Before the microporous solid phase material of Formula 1 can be used for diagnostics tests, including lateral flow applications, it is conjugated to a molecule of interest (designated here as Q). The molecule Q generally contains a free primary or secondary amine group, or is a molecule to which an amino group has been covalently attached. The molecule Q can be bonded directly to the solid phase material of Formula 1 by blotting or directly applying Q in a solution, generally an aqueous solution, to the derivatized material of Formula 1 to form the conjugate of Formula 3. After the molecule of interest, Q, has bonded to the solid phase material of Formula 1, any unreacted sites on the derivatized solid phase material may be blocked with a blocking agent (designated here as Q'). Suitable blocking agents are tris(hydroxymethyl)aminomethane (NH2C (CH2OH)3) or a protein other than the molecule of interest, for example, casein or bovine serum albumin. The reaction between the molecule of interest, Q, and the derivatized material of Formula 1 is illustrated by the chemical scheme shown immediately

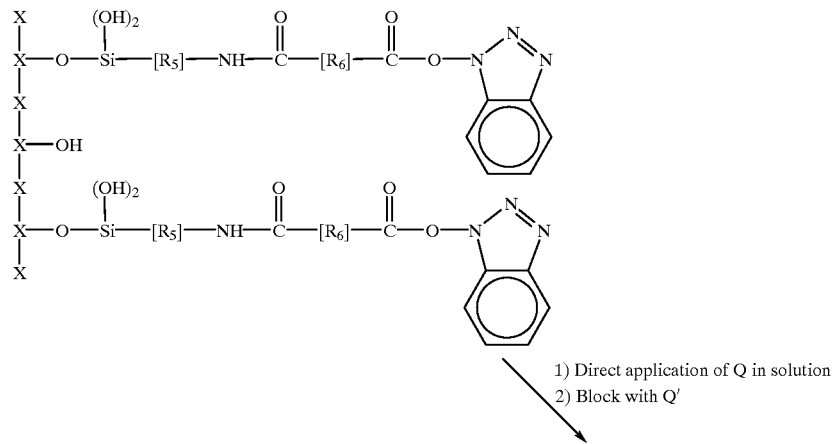

1) Direct application of Q in solution
2) Block with Q'

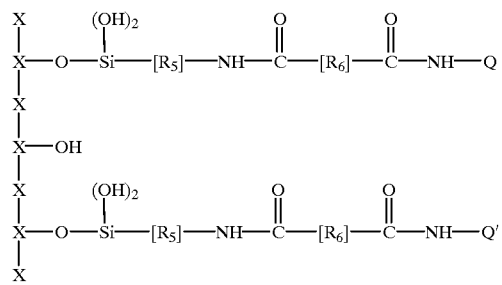

Once the conjugate of Formula 3 is prepared as described and illustrated above, the conjugated Q and solid phase material may be dried. Once the conjugate is dry, it may be washed with an aqueous buffer to remove unreacted materials, and dried again before the conjugate is stored for later use in diagnostics tests, including lateral flow applications as discussed below.

Before the microporous solid phase material of Formula 2 can be used for diagnostics tests, including lateral flow applications, it is conjugated to a molecule of interest (designated here as L) that contains a sulhydryl group or to which a sulfhydryl group has been covalently attached. The molecule L can be bonded directly to the solid phase material of Formula 2 by blotting or directly applying L in solution, such is an aqueous solution, to the derivatized material of Formula 2 to form the conjugate of Formula 4. After the molecule of interest, L, has bonded to the solid phase material of Formula 2, any unreacted sites on the derivatized solid phase material may be blocked with a blocking agent (designated here as L'). Suitable blocking agents include cysteine or a protein other than the molecule of interest, for example, casein or bovine serum albumin. The reaction between the molecule of interest, L, and the derivatized material of Formula 2 is illustrated by the chemical scheme provided immediately below.

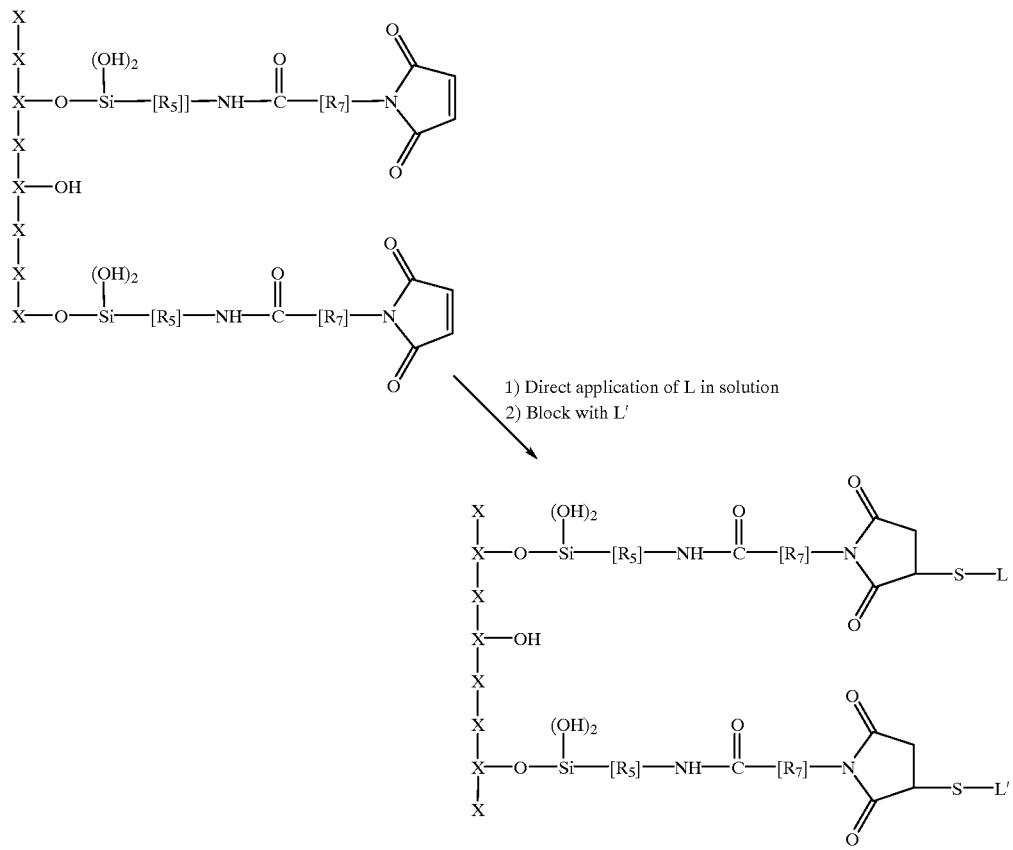

The examples provided herein are offered solely for illustration and not limitation.

C. Examples

EXAMPLE 1

Activation of Nitrocellulose with HBT

Preparation of Aminosilylated Nitrocellulose

A nitrocellulose strip (24×2.5 cm) was placed in 100 ml of a 5% solution of 3-aminopropyltriethoxysilane (pH 3.0) and allowed to react at room temperature for 2 hours with shaking. The nitrocellulose strip was removed from the solution and washed twice with 10 mM sodium phosphate buffer (pH 8.0) containing 0.01% Tween 20. It was then dried at 50° C.

Activation of Aminosilylated Nitrocellulose with Succinic Anhydride and HBT

The amino silylated nitrocellulose strip was placed in 100 ml of a 1 mg/ml succinic anhydride solution (pH 8.1) and allowed to react at 35° C. for 2 hours. The nitrocellulose strip was then removed, washed twice with deionized water and dried. The nitrocellulose strip was then placed in 100 ml of deionized water and 100 μl of HBT (50 mg dissolved in 100 μl of DMF) was added, followed by the addition of 100 μl of an EDAC solution (20 mg dissolved in 100 μl of deionized water). The solution containing the strip was mixed well by stirring and then stored overnight at 5° C. The nitrocellulose strip was removed from the solution, washed twice with deionized water and dried. The strip was treated with 3 μl/mm² of 0.04% Tween 20 and dried at 50° C. for 5 minutes. The activated nitrocellulose strip was stored at room temperature in a sealed container for later use.

EXAMPLE 2

Activation of Nitrocellulose with Succinic di-HBT

Preparation of Succinic di-HBT

Succinic acid (0.35 g, 3 mmol) and HBT (1.5 g, 11 mmol) were dissolved in 5 ml of DMF. After cooling the mixture to 5° C., 0.75 ml of DICD was added dropwise. The mixture was allowed to react at 2–5° C. for 4 hours. After centrifuging the mixture at 10,000×g for 15 minutes, the supernate was transferred and diluted with DMF to give a 5 ml solution (approximately 100 mg succinic di-HBT/ml). The succinic di-HBT was diluted to 1 mg/ml with 10 mM phosphate buffered saline (pH 8.0).

Activation of Aminosilylated Nitrocellulose with Succinic di-HBT

The aminosilylated nitrocellulose strip (prepared as described in Example 1) was added to 5 ml of the 1 mg/ml succinic-HBT solution and allowed to react for 1 hour at 20° C. The strip was then removed from the succinic-HBT, washed with 3×10 ml of deionized water and dried. The strip was treated with 3 μl/mm² of 0.04% Tween 20 and dried at 50° C. for 5 minutes. The activated nitrocellulose was stored at room temperature in a sealed container for later use.

EXAMPLE 3

Activation of Glass Fibers with Succinic di-HBT

An aminosilylated glass fiber pad (24×2.5 cm) was prepared as described for nitrocellulose in Example 1. The aminosilylated glass fiber pad was then activated with succinic di-HBT as described in Example 2.

EXAMPLE 4

Covalent Bonding of Streptavidin-FITC to Activated Nitrocellulose

Activated nitrocellulose (prepared as described in Example 1) was cut into 15×5 mm pads. 15 μl of 1.0, 0.5, 0.25, and 0.125 mg/ml of fluoroscein isothiocyanate-labeled streptavidin (SA-FITC) in 5 mM phosphate buffer (pH 8.0) was added to each nitrocellulose pad, corresponding to 200, 100, 50, 25 ng/mm$^2$ of SA-FITC added to each pad respectively. The pads containing the SA-FITC were allowed to react at room temperature for 1 hour. The pads were then washed 4 times by sonicating for 30 seconds in 20 ml of 10 mM NaCl containing 0.01% Tween 20. To check for passive absorption, one set of pads were each treated with 0.25 ml of 1% SDS and sonicated for 60 seconds. Another set of pads were hydrolyzed with 0.01 N NaOH at 38° C. for 2 hours, followed by sonicating for 30 seconds to determine covalent bonding. The solution from each pad was diluted and the concentration of SA-FITC determined. The recovery of the passively adsorbed and covalently bonded SA-FITC from the nitrocellulose (summarized in Table 1) indicates that the mode of attachment is primarily covalent.

TABLE 1

Recovery of SA-FITC From Passive Adsorption and Covalent Bonding on Nitrocellulose
SA-FITC (ng/mm$^2$)

| applied | Passive | covalent |
|---|---|---|
| 25 | 2.2 | 11.7 |
| 50 | 2.8 | 28.7 |
| 100 | 4.3 | 39.7 |
| 200 | 4.7 | 42.7 |

EXAMPLE 5

Covalent Bonding of Human IgG-FITC to Activated Glass Fiber

Activated glass fiber (di-HBT) was prepared as described in Example 3. Solutions of fluorescein isothiocyanate-labeled human IgG (hIgG-FITC) at varying concentrations (0.3, 0.6, and 1.5 mg/ml) were applied in 25 μl aliquots to 15×5 mm pieces of the activated glass fiber. After incubation at room temperature for 2 hours, the pads were washed with phosphate buffered saline (pH 7.4) containing 0.01% Tween 20 and dried. To check for passive adsorption, one set of pads was each treated with 0.25 ml of 1% SDS and sonicated for 60 seconds. Another set of pads was hydrolyzed with 0.01 N NaOH at 38° C. for 2 hours, followed by sonicating for 30 seconds to determine covalent bonding. The solution from each pad was diluted and the concentration of hIgG-FITC determined. The recovery of the passively adsorbed and covalently bonded hIgG-FITC from the glass fiber (summarized in Table 2) indicates that the primary mode of attachment is covalent.

TABLE 2

Recovery of hIgG-FITC From Passive Absorption and Covalent Bonding on Glass Fibers
hIgG-FITC (ng/mm$^2$)

| applied | passive | covalent |
|---|---|---|
| 100 | 7.6 | 48.1 |
| 200 | 4.7 | 46.2 |
| 500 | 10.1 | 54.8 |

EXAMPLE 6

Covalent Bonding of Biotin to Activated Nitrocellulose

Preparation of the Succinic di-HBT Activated Nitrocellulose Membrane

A solution (pH 3.0) of 5% aminosilane in deionized water was prepared the day of use. A nitrocellulose membrane was laminated onto a PVC card and the card was placed in 100 ml of the above solution for 2 hours at room temperature. The card was removed from the solution and dried for 15 minutes in a drying oven at 37° C. The dried card was washed twice with 50 ml of 10 mM phosphate buffer (pH 8.0) containing 0.02% Bioterge. The card was then placed in 100 ml of succinic di-HBT (40 μg/ml) in 10 mM phosphate buffer (pH 8.0) containing 0.02% Bioterge and washed for two hours on a rotator. After rinsing 2 times (5 minutes each) in 10 mM phosphate buffer (pH 8.0) containing 0.04% Bioterge and 0.04% Tween 20, the cards were dried for 15 minutes in a drying oven at 37° C.

Biotin Amine Strip Preparation

Using a BioDot XY-3000 Sprayer, a biotin-cadaverine solution (17 μg/ml in 10 mM phosphate buffer (pH 8.0) was sprayed in 4 bands on the di-succinic HBT activated nitrocellulose membrane. Each band was sprayed at 0.625 μl/cm with a drop size of approximately 20 nanoliters. After spraying, the card containing the nitrocellulose membrane was dried for 15 minutes in a drying oven at 37° C. The nitrocellulose membrane was then blocked by wetting the membrane with 50 mM Tris for 1 hour. After blotting the excess Tris from the membrane, the card (with attached membrane) was washed two times, for a minimum of 5 minutes, in 50 mM phosphate buffer containing 0.02% Bioterge. The card was then dried for 15 minutes in a drying oven at 37° C. A collection pad, blocked with 10 mM sodium tetraborate buffer (pH 8.6), was attached to the bottom of the card. Wicking paper was attached to the top of the card. After assembly, the completed card was cut with a BioDot cutter to 5 mm widths and the strips stored in plastic bags with desiccant.

Test Procedure

To each of two 12×75 mm borosilicate test tubes was added 110 μl of 10 mM phosphate buffer (pH 8.0, containing 4% sucrose and 0.5% BSA). A control sample was prepared by adding 5 μg of colloidal gold BSA-biotin (1.25 μl of a 4 mg/ml solution) to one tube. A test sample was prepared by adding 5 μg of colloidal gold streptavidin (1.25 μl of a 4 mg/ml solution) to the other tube. A test strip was placed into each tube and allowed to develop for 15 minutes. The developed test strips were removed from the tubes, dried and read on a Minolta CR-241 strip reader. The results summarized in Table 3 indicate that biotin, a small molecule (molecular weight 244), was immobilized on the strips.

TABLE 3

Comparison of Color Intensities of Bands on Strip
for Test and Control Samples
Color Intensity

| Band | Test | Control |
|------|------|---------|
| 1 | 8.05 | 6.71 |
| 2 | 7.87 | 1.72 |
| 3 | 7.39 | .050 |
| 4 | 7.19 | 0.61 |

EXAMPLE 7

Stability of Nitrocellulose Strips Containing
Covalently Bound Antibody

Preparation of Nitrocellulose with Covalently Bound Antibody

A nitrocellulose membrane (25.4×300 mm) was laminated onto a 70×300mm PVC card and then activated with succinic di-HBT as described in Example 6. Six lines of a 2 mg/ml goat-anti-mouse antibody, in 150 mM phosphate buffer (pH 7.4), were applied to the membrane with a BIODOT XY-3000. Each line was applied at approximately 0.625 μl/cm. After drying in an oven at 37° C. for 15 minutes, the membrane was blocked by wetting with 50 mM Tris (pH 8.0) for 1 hour. The membrane was then washed in a 50 mM phosphate buffer (pH 8.0) containing 0.02% Bioterge, 2 times for a minimum of 5 minutes each, and dried in an oven at 37° C. for 15 minutes.

Preparation of Nitrocellulose with Passively Bound Antibody

A nitrocellulose membrane was laminated onto a PVC card, as described above, but not activated. Six lines of a 2 mg/ml goat-anti-mouse antibody solution were applied to the membrane as described above. Immediately after application of the lines, the membrane was blocked by using the BioDot XY-3000 airjet to apply a 150 mM phosphate buffered saline solution (pH 7.4) containing 0.5% BSA and 4.0% sucrose. The membrane was then dried in an oven at 37° C. for 15 minutes.

Assembly of the Test Strips

Absorbent paper (previously treated with a blocking solution containing 100 mM sodium phosphate and 1% Triton X-100, pH 7.4, and then dried) was laminated to the upstream side of the PVC card containing the passively bound nitrocellulose. Absorbent paper (previously treated with a blocking solution containing 100niM sodium borate and 1% Triton X-100, pH 7.4, and then dried) was laminated to the upstream side of the PVC card containing the covalently bound nitrocellulose. Untreated absorbent paper was laminated to the downstream sides of each card. All absorbent paper was applied to form a 2 mm overlap with the top and bottom edges of the nitrocellulose. The laminated cards were cut into 5 mm wide strips. The strips were stored at room temperature in tubes with desiccant.

Test Procedure

Test strips from each group were placed in a closed humidity chamber with a small amount of water in the bottom of the chamber and incubated at 37° C. Following 24 hours of incubation, one strip from each test group was removed from the humidity chamber and dried for 15 minutes at 37° C. The test strips, along with control strips not exposed to humidity, were tested as described below.

Sample diluent (100 μl of 0.7% sodium phosphate buffer, pH 7.4, containing 1.0% BSA and 0.1% sodium azide) and 5 μg of colloidal gold/streptavidin (50 μl of a 100 μg/ml solution in sample diluent) were added to a 12×75 mm borosilicate tube for each of the strips to be tested. While vortexing, 600 ng of mouse IgG-biotin (15 μl of a 40 μg/mL solution in sample diluent) was then added. The solution was then brought to 120 μl with the sample diluent. Strips were then inserted (one strip per tube) into the tube containing the test solution, incubated for 15 minutes and analyzed for total color of test lines using a Minolta CR-241 strip reader. The results, summarized in Table 4, indicate that the strips with covalently bound antibody were more stable than the strips with passively bound antibody when exposed to moisture for 24 hours.

TABLE 4

Comparison of Total Color Intensities of Bands
for Covalent and Passive Test Strips Exposed to Moisture

| Incubation Time (hrs) | Total Color Intensity | |
|---|---|---|
| | Covalent | Passive |
| 0 | 367.6 | 321.2 |
| 24 | 314.2 | 231.8 |
| (% Loss) | (14.5) | (27.8) |

II. Lateral Flow Devices

The materials described above can be used to make a variety of products and devices. One example is a single or multiple analyte semi-quantitative/quantitative rapid diagnostic lateral flow test system. The system provides improved immunological and other specific binding assay methods and devices in a single or multi-analyte format, using background and contrast reagents in an LFD to instrumental or non-instrumental visual endpoints.

A. Sandwich LFD With Single Test Line

A sandwich format lateral flow device ("LFD") with a single test line for the determination and semi-quantitative detection of a large molecule analyte in an aqueous sample is illustrated in FIG. 1. The various dimensions are not necessarily drawn to scale in any of the Figures.

The LFD 10 includes a porous membrane 12 made, for example, of nitrocellulose, glass fiber, or nylon. Other appropriate membrane materials can be used depending on the characteristics of pore size, binding capacity, the particular aqueous sample and assay procedure. Usually, the porous membrane 12 can have a pore size between 2 and 10 microns. In a useful form, the porous membrane 12 will have a length between approximately 50–100 mm and a width between approximately 3.5–8.0 mm. The porous membrane 12 also will have a thickness, for example, between approximately 50–300 microns and a capillary rise characteristic, relative to an aqueous solution, between approximately 10–50 mm/min. However, the specific characteristics and dimensions of the porous membrane 12 are not critical and may be modified as necessary to achieve desired results of speed and a positive test result.

As vshown in FIG. 1, a wicking pad 14 overlaps the porous membrane 12 at one end 16 of membrane 12 such that it is in liquid transfer contact with the porous membrane 12. The wicking pad 14 can be made of glass fiber, fibrous cellulose or other suitable materials. The dimensions of the wicking pad 14 usually are not critical and usually are between 20–50 mm in length, between 3.5–8 mm in width and 0.5–2.0 mm in thickness.

The LFD 10 includes a conjugate zone 18. The conjugate zone 18 can be a region of the wicking pad 14 or the porous membrane 12 or one or more separate reagent pads that are in liquid transfer contact with the wicking pad 14 or porous membrane 12. The wicking pad 14, porous membrane 12 and conjugate zone 18 can be held in place by a strip of tape (not shown). In other embodiments, the wicking pad 14, porous membrane 12 and conjugate zone 18 can be held in place by an adhesive material or by the natural constriction of a container (not shown) housing the LFD components and preventing their contamination.

The conjugate zone 18 contains two reagents. The first reagent is a contrast reagent that is attached to a portion or fragment of the large molecule analyte of interest (referred to herein as the "α-region-fragment") by covalent or ionic binding, adsorption or other means of attachment known in the art to form a contrast binding ligand (CL). The CL can be dried, reconstitutable, liquid-dispersible, diffusible, colored-latex beads. Usually, the latex beads are light in color; for example, yellow. Instead of colored-latex beads, the background reagent can be a colored dye molecule, an enzyme and dye combination, or a fluorescent, luminescent or radioactive molecule.

The second reagent contained in the conjugate zone 18 is a dried, reconstitutable, liquid dispersible, diffusible indicator reagent that is attached to a binding ligand specific for a second region ("β-region") of the large molecule analyte of interest to form an indicator binding ligand (IL). The α-region-fragment and β-region of the large molecule analyte must be separate non-cross-reacting units. The indicator reagent can be colloidal gold particles, enzyme/dye combinations, colored latex particles, carbon particles, or fluorescent, luminescent or radioactive particles that can be visibly or otherwise distinguished from the CL.

One or both of the first and second reagents can be uniformly impregnated or dispersed within the conjugate zone 18 before they are contacted by the aqueous sample. Alternatively, for example, the conjugate zone 18 can be coated with one or both reagents and the reagents dispersed throughout the conjugate zone when contacted by the aqueous sample. Or the two reagents can be longitudinally spaced apart within the conjugate zone 18 and dispersed throughout the conjugate zone when contacted by the aqueous sample.

As shown in FIG. 1, the LFD 10 includes an absorption pad 30 at the second end 32 of the porous membrane 12 opposite the wicking pad 14. Between the absorption pad 30 and the conjugate zone 18 are one test line 22, a space 20 between the conjugate zone 18 and the test line 22, and a second space 24 between the test line 22 and absorption pad 30. The test line 22 is located on the porous membrane 12 and contains an immobilized binding ligand specific for the α-region-fragment of the analyte of interest.

The absorption pad 30 can be a glass fiber or fibrous cellulose pad or other suitable material in liquid transfer contact with the porous membrane 12. The absorption pad 30 collects unreacted reagent and sample and acts as a wick to remove any background material from the test line 22.

A test sample containing an analyte moves along the wicking pad 14, shown in FIG. 1, to the conjugate zone 18 by capillary action. When the sample comes into contact with the IL in the conjugate zone 18, it reacts to form an analyte-IL complex. The CL attached to the α-region-fragments moves along the wicking pad with, but does not react with, the analyte or the analyte-IL complex.

When the aqueous sample's fluid front reaches the test line 22, a competition for the immobilized α-region-specific ligand's binding sites occurs among the CL, analyte-IL complexes, and uncomplexed analyte. For purposes of illustration only, for the following example, the contrast reagent is yellow latex beads and the indicator reagent is colloidal gold particles. When no analyte is present in the aqueous sample, only α-region-fragments-yellow latex beads (CL) will attach to the α-region-fragment-specific ligands immobilized on test line 22 and test line 22 will appear yellow. When there is a small concentration of analyte in the sample, the CL and IL will compete for the limited number of binding sites on the α-region-fragment-specific ligand immobilized on the test line 22, with the yellow-colored beads predominating over the red of the colloidal gold complex forming a brown color. As the concentration of analyte increases, the concentrations of analyte-IL complexes increases and competes more effectively for the limited number of α-region-fragment-specific ligand binding sites, and the test line 22 will become more red in color.

The above-described transition in color in the test line 22 from yellow-to-brown-to-red forms the basis of a semi-quantitative single line test. Comparable transitions can be achieved by substituting other contrast and indicator reagents for the latex beads and colloidal gold. In each case, a visual or otherwise detectable test line 22, or color signal transition for multiple regions, will develop whether the test is negative or positive and will serve as a procedural control for test validity.

After moving into the test line 22, any unbound sample constituents and reagents continue to move up the porous membrane 12 into the absorption pad 30, which acts as a wick to pull sample upward, thus washing out the test line 22 area of any background material.

B. Sandwich LFD With Capture Region

For analytes that occur in high concentrations, the range over which the analyte is determined can be increased by preparing a capture region that intercepts a portion of the analyte prior to the sample reaching the test line 22 in FIG. 1. A capture antibody or other capture molecule can be attached to the wicking pad 14 or, for example, in space 20 on porous membrane 12 by known methods. The capture molecule lowers the concentration of analyte in a test aqueous sample by removing a fraction of the analyte and, thereby, extends the range of the color or other signal transition zone detected at test line 22. The fraction of the analyte removed in the capture zone can be empirically established during manufacturing and quality control procedures for the LFD 10 and specific analyte.

The AMZ is described in greater detail in Example 8 for a sandwich LFD with a single test line, where an AMZ has extended the range of the test. The AMZ also can be used and applied to other sandwich LFD formats.

C. Sandwich LFD With Reference Line

Figure 3:
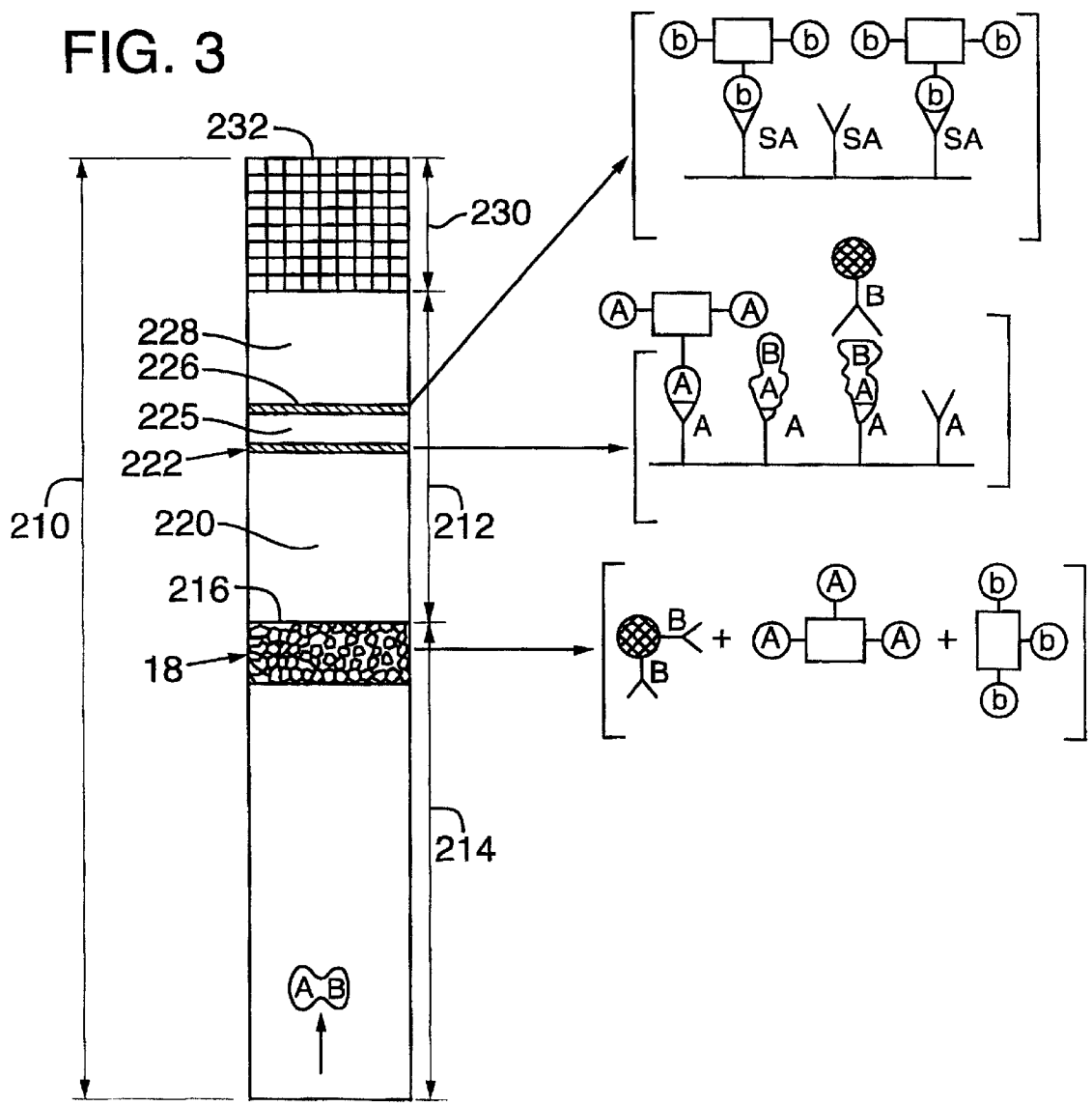
FIG. 3 is a schematic representation of an alternative embodiment of a sandwich format LFD that includes a reference line.

The sandwich format LFD 10 of FIG. 1 also can be modified to accommodate a reference line 226 as shown in FIG. 3. Functionally, the reference line 226 provides a check for samples containing very low amounts of analyte.

Structurally, the LFD 210 of FIG. 3 differs for the LFD 10 for FIG. 1 in the following ways. There are two separate species of background reagents used in the conjugate zone 218. The first species is the CL of the analyte of interest described above for FIG. 1. The second species is created by attaching the contrast reagent to a capturable label that has a specific capturing binding partner. One example of such a capturable label and capturing binding partner is biotin and streptavidin. Other suitable labels and binding partners are known in the art and can be incorporated by standard methods.

The capturing binding partner is immobilized on the porous membrane 212 to form a reference line 226. The reference line 226 is located at the second end 232 of the porous membrane 212 between the conjugate zone 218 and the absorption pad 230. The reference line 226 usually is distanced from the conjugate zone 218 by approximately 2–4 mm and absorption pad 230 by approximately 5–50 mm to create a first space 224 and second space 228 on the porous membrane 212.

When the sample moves up the porous membrane 212 from the conjugate zone 218, the background reagents will travel with it. The contrast reagent attached to the α-region-fragment will compete for immobilized α-region-fragment-specific ligand binding sites on ATZ 222 with analyte-IL complexes as described for FIG. 1. The contrast reagent attached to the capturable label will bind to the capturing binding partner immobilized at the reference line 226.

For purposes of illustration only, for the following that contrast reagent is yellow latex beads and the indicator reagent is colloidal gold particles. If there is no analyte in the sample, the color of the reference line 226 and test line 222 will be the same color. When there is analyte in the sample, the reference line 226 will be yellow while the test line 222 will be brown-to-red in color, depending on the concentration of analyte in the sample. The color of the reference line 226 thus provides a basis for color comparison with the color of the test line 222. Comparable reference line and test line comparisons can be achieved with other contrast and indicator reagents.

D. Sandwich LFD With Multiple Test Lines

Figure 2:
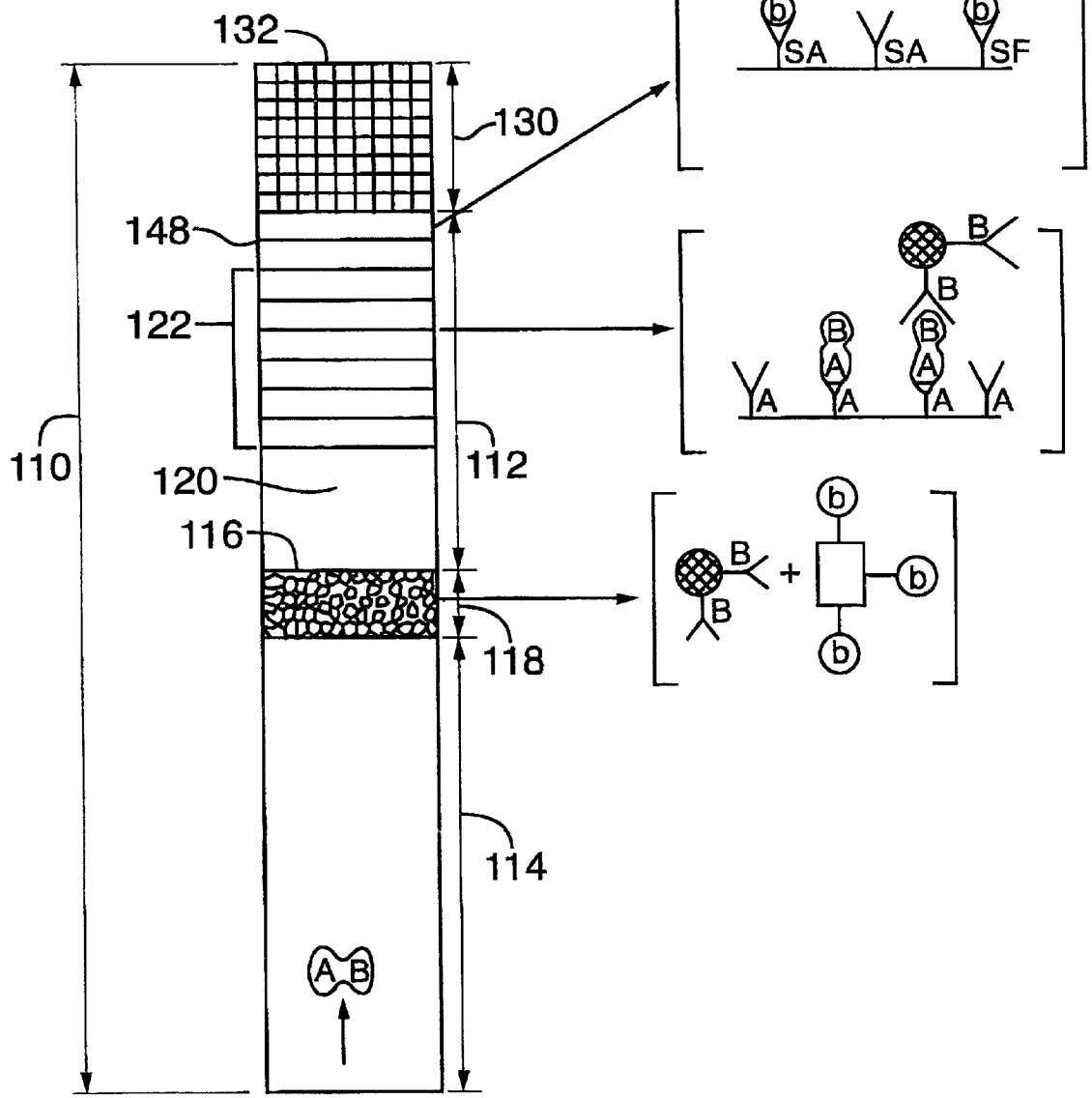
FIG. 2 is a schematic representation of a sandwich format LFD with multiple test lines that is compatible with semi-quantitative detection of large molecule analytes. This particular format includes a control line.

A sandwich LFD format with multiple parallel test regions for the determination and titration of an immunologically reactive large molecule analyte in an aqueous sample is illustrated in FIG. 2. This format enables the user to determine zero, from lower and higher concentrations of analyte, by the use of a scale to correlate the location of a color transition zone. The test lines that develop are detectable on the porous membrane due to binding of the analyte-IL complex to the limited number of immobilized binding sites on the ATZ.

Using multiple parallel test lines allows for a titration of the analyte concentration. Zero or subthreshold levels of analyte will not form lines within the matrix. Small amounts of IL will be completely captured by the first or second line. Larger amounts of analyte will be captured by subsequent lines as the analyte sequentially saturates the binding sites. The analyte, therefore, is quantitated by the color signal transition pattern.

The LFD 110 includes a porous membrane 112 made of nitrocellulose, glass fiber, nylon or other suitable materials. The specific dimensions of the porous membrane 112 are not critical and maybe modified as necessary to achieve desired results of speed and positive test results.

As shown in FIG. 2, a wicking pad 114 overlaps the porous membrane 112 at one end 116 of membrane 112 such that it is in liquid transfer contact with the porous membrane 112. The wicking pad 114 can be made of glass fiber, fibrous cellulose or other suitable materials.

The LFD 110 includes a conjugate zone 118. In FIG. 2, as in FIG. 1, the conjugate zone 118 can be either a region of the wicking pad 114 or porous membrane 112 or one or more separate reagent pads in liquid transfer contact with the wicking pad 118 or porous membrane 112. The wicking pad 114, porous membrane 112 and conjugate zone 118 can be held in place by a variety of methods known in the art.

The conjugate zone 118 contains two reagents. The first reagent is a labeled control reagent. It, for example, can be dried, colored, liquid dispersible, diffusible latex beads. The label is one that has a specific binding partner, e.g., biotin and streptavidin. The beads are usually light in color; for example, yellow. As an alternative to colored-latex beads, the control reagent may be a light-colored dye molecule, an enzyme and dye combination, or a fluorescent, luminescent or radioactive molecule.

The second reagent contained in the conjugate zone 118, is a dried, reconstitutable, liquid dispersible, diffusible indicator reagent that is attached to a binding ligand specific for a region ("β-region") of the large molecule analyte of interest. The indicator reagent can be colloidal gold particles, enzyme/dye combinations, colored latex particles, carbon particles, or fluorescent, luminescent or radioactive molecules that can be visibly or otherwise distinguished from the control reagent.

One or both of the first and second reagents can be uniformly impregnated or dispersed within the conjugate zone 118 before they are contacted by the test sample. Alternatively, for example, the conjugate zone 118 can be coated with one or both reagents and the reagents dispersed throughout the conjugate zone when contacted by the sample. Or the two reagents can be longitudinally spaced apart within the conjugate zone 118 and dispersed throughout the conjugate zone when contacted by the sample.

As shown in FIG. 2, the LFD 110 includes between 2 and 20, usually about 7, multiple test lines 122, a space 120 between the conjugate zone 118 and the test lines 122, and a space 124 between the test lines 122 and an absorption pad 130 at the second end 132 of the porous membrane 112. The test lines 122 contain a binding ligand specific for a second region (α-region) of the analyte of interest that is immobilized on the porous membrane 112. The α- and β-regions of the large molecule analyte must be separate non-cross-reacting units.

A control line 148 is located on the porous membrane 112 near end 132. The control line 148 contains an immobilized binding partner (e.g., streptavidin) for the label attached to the background reagent (e.g., biotin).

The absorption pad 130 can be glass fiber, fibrous cellulose or other suitable material in liquid transfer contact with the porous membrane 112. The absorption pad 130 collects unreacted reagent and sample constituents and acts as a wick to remove any background material from the test lines 122.

A test sample containing an analyte moves along the wicking pad 114 of FIG. 2 to the conjugate zone 118 by capillary action. When the sample comes into contact with the IL in the conjugate zone 118, it reacts to form an analyte-IL complex. The labeled control reagent moves along the wicking pad 114 with, but does not react with, the analyte-IL complex or IL. When the sample's fluid front reaches the test lines 122, only the analyte-IL complex and any uncomplexed analyte will bind to the α-region-specific ligand immobilized on test lines 122.

For purposes of illustration only, for the following the background reagent is yellow latex beads and the contrast reagent is colloidal gold particles. When there is no analyte, no test lines have color or are otherwise visible. As the concentration of analyte increases in the aqueous sample, the concentration of analyte-IL complexes increases and saturates the limited number of α-region-specific ligand binding sites at test lines 122, creating a situation where more of the test lines 122 will become red in color.

The labeled yellow-colored latex beads will continue to migrate and then react with the label's binding partner immobilized on control line 148. The control line 148 will be colored both in the presence and absence of analyte. The color of the control line 148 will be distinct from the test lines 122. After moving through the test lines 122 and control lines 148, the sample continues to move up the porous membrane 112 onto the absorption pad 130 which collects unreacted reagents and sample and acts as a wick to remove from the test line area 122 any background material.

Examples of the above described LFDs used to d etect hCG in urine samples are found in Examples 8, 9, and 10 below.

Multiple test lines in the ATZ (as shown in FIG. 2, area 122) could be used in the format of FIGS. 1 and 3 and the resulting color or signal transition pattern in the ATZ is then compared with that of patterns from known analyte concentrations.

EXAMPLE 8

Sandwich LFD With Single Test Line
Preparation of Test Strips

Pregnancy test strips (SA Scientific, San Antonio, Tex.) containing dried anti-beta hCG monoclonal antibody conjugated to colloidal gold on a glass fiber conjugate pad were obtained. These strips contained immobilized anti-α hCG on a test line and immobilized anti-mouse IgG on a control line on a nitrocellulose membrane similar to what is depicted in FIG. 1. The conjugate pad was carefully removed intact using a razor blade. To the region of nitrocellulose membrane corresponding to space 20 in FIG. 1, varying amounts of monoclonal anti-β hCG capture antibody (0, 250, 500, 10 00, 2000 ng) were added, dried, washed and dried again.

The conjugat e pad was carefully and uniformly coated with a total of 3 μl (in 0.2 μl drops) of a 10 mg/ml solution of yellow latex beads (200 nm particles, carboxylated) covalently conjugated with affinity purified α-region of hCG (20 ng/mg latex). The pad was then dried at 50° C. The conjugate pad was then placed back in its original position on the modified test strip and secured with cellophane tape.

Test Procedure

Negative urine samples were spiked with hCG to achieve concentrations of 0, 25, 225, 450, 1100, 2500, 10,000 and 100,000 mIU/ml. A 0.3 ml aliquot from each of the 8 spiked urine samples was added to separate microfuge tubes. The wicking pad of each test strip was placed in contact with the urine. Each strip contained a set amount of immobilized capture antibody and a conjugate pad as described above.

After five minutes, the ATZ on each test strip was then visually scored for color type as either yellow (Y), brown (B), red-brown (RB), or red (R). The test results are summarized in Table 5.

The results in Table 5 show a semi-quantitative capability arising from the use of a yellow-colored latex and red colloidal gold combination. The results also show that there is an improvement in the range of concentrations indicated by the brown-colored line achieved by removing excess hCG at the higher immobilized anti-β monoclonal antibody levels in the AMZ. The additional antibody did not compromise sensitivity, and there were no false positives due to non-specific binding of the colloidal gold to the test line. At 1000 and 2000 ng of anti-β hCG capture antibody, the brown color extended to 1000 mIU/ml, which is 3–5 times higher than the range seen in the control, 0 ng, antibody strips.

EXAMPLE 9

Sandwich LFD With Reference Line
Preparation of Reference Line Test Strips

The preparation pregnancy strips (SA Scientific, San Antonio, Tex.) with reference lines containing immobilized streptavidin required temporary removal of the conjugated pads from the pregnancy strips to avoid damaging the pads during preparation of test strips corresponding to FIG. 3. While each conjugate pad was removed, a coating of 3 μl biotin-labeled yellow latex beads (10 mg/ml) and yellow latex beads covalently conjugated with α-region-fragments of hCG (10 mg/ml) were added to the reagent pad as described above in Example 8.

The reference line 226 can be prepared by immobilizing streptavedin directly on the porous membrane using passive adsorption or other methods known in the art.

Test Procedure

Test procedures were identical to those in Example 8, except that only 0, 25, and 10,000 mIU/ml samples were tested.

Test Results

In the negative sample, the yellow color in the test line 222 was indistinguishable from the reference line 226. The 25 mIU/ml sample displayed a weak brown color relative to the yellow reference line. The 10,000 mIU/ml sample yielded a solid red test line and a yellow reference line.

EXAMPLE 10

Sandwich LFD With Multiple Test Line ATZ
Preparation of Test Strips

Custom test strips corresponding to FIG. 2 were prepared that contained 7 anti-α hCG antibody test lines spaced 1 mm apart on the nitrocellulose membrane. A line of streptavidin was immobilized on the control line 148 as described for the reference line 226 in Example 9.

Yellow latex-BSA conjugated with biotin (3 ml at 10 mg/ml) was added to the anti-β hCG monoclonal antibody-colloidal gold treated conjugate pad and air dried. The pad was secured to the test strips with cellophane tape to the backing.

Seven test lines 122 were prepared as described for test lines 22 in Example 8.

Test Procedure

The following procedure was performed in triplicate using the test strips prepared above. The strips were placed in 0.5 ml of hCG negative urine that had been spiked with varying amounts of hCG (0–51, 200 mIU/ml). The strips were allowed to develop for 10 minutes. The strips were then dried for 2 hours, at 50° C. and color intensity determined on a calorimeter using the Yxy color field (Minolta CR-241, 0.3 discrimination aperture). The signal intensities were then calculated using the sum of the first four lines (net 1–4) for the Y color space. The data is presented in Table 6. A plot was then made correlating the Net 1–4 with the log hCG concentration, shown in FIG. 4. A linear least squares fit was derived and values were calculated from that fit for each hCG concentration tested, and compared to the known values (Table 7). A visual discrimination of the line number containing the last visible red line was also performed on the test strips developed above. The results were summarized in Table 8, and the averages were plotted in FIG. 5.

Test Results

The multi-test line format allows for quantitating the level of hCG in urine. Calculated values differed from known values on average by 13%, with a range of from 0.6–26.3%. A visual semi-quantitative method allows the user to place the hCG concentration into 5–7 ranges of hCG within a range of 50 mIU/ml to greater than 50,000 mIU/ml.

TABLE 5

| | anti-beta hCG capture mAb immobilized | | | | |
|---|---|---|---|---|---|
| MIU/ml hCG | 0 ng | 250 ng | 500 ng | 1000 ng | 2000 ng |
| 0 | Y | Y | Y | Y | Y |
| 25 | B | B | B | B | B |
| 225 | B | B | B | B | B |
| 450 | R | RB | RB | B | B |
| 1100 | R | RB | R | RB | RB |
| 2500 | R | R | R | R | R |
| 10,000 | R | R | R | R | R |
| 100,000 | R | R | R | R | R |

TABLE 6

| | Strip | | | | | | | | | | | |
|---|---|---|---|---|---|---|---|---|---|---|---|---|
| Line | 1 | 2 | 3 | 4 | 5 | 6 | 7 | 8 | 9 | 10 | 11 | 12 |
| 1 | 90.19 | 84.83 | 75.14 | 66.59 | 40.86 | 29.92 | 34.01 | 27.76 | 16.19 | 15.78 | 23.76 | 19.15 |
| 1 | | 83.98 | 75.23 | 71.24 | 55.68 | 43.1 | 41.3 | 23.74 | 22.68 | 20.92 | 21.56 | 15.85 |
| 1 | | 84.43 | 75.06 | 55.39 | 57.77 | 47.08 | 35.69 | 31.55 | 26.71 | 18.24 | 22.12 | 19.92 |
| 1 ave | 90.19 | 84.41 | 75.143 | 64.41 | 51.44 | 40.03 | 37 | 27.68 | 21.86 | 18.313 | 22.48 | 18.31 |
| 2 | 89.7 | 91.99 | 87.34 | 86.9 | 76.62 | 71.4 | 69.63 | 56.71 | 42.97 | 50.77 | 41.73 | 19.14 |
| 2 | | 89.65 | 86.71 | 85.54 | 83.53 | 75.26 | 75.41 | 58.43 | 55.34 | 44.94 | 34.6 | 24.47 |
| 2 | | 87.68 | 88.23 | 88.69 | 81.89 | 76.73 | 72.33 | 63.66 | 58.68 | 52.19 | 35.24 | 22.13 |
| 2 ave | 89.7 | 89.77 | 87.427 | 87.04 | 80.68 | 74.46 | 72.46 | 59.6 | 52.33 | 49.3 | 38/10 | 21.91 |
| 3 | 89.25 | 88.32 | 87.9 | 87.56 | 84.09 | 81.26 | 80.88 | 73.47 | 72.46 | 71.29 | 60.04 | 37.03 |
| 3 | | 89.64 | 87.25 | 87.78 | 85.7 | 87.09 | 83.17 | 82.61 | 74.98 | 66.3 | 53.23 | 40.99 |
| 3 | | 87.54 | 87.65 | 89.65 | 86.06 | 83.98 | 81.52 | 77.9 | 73.01 | 70.8 | 55.12 | 36.21 |
| 3 ave | 89.25 | 88.5 | 87.6 | 88.33 | 85.28 | 84.11 | 81.86 | 77.99 | 73.48 | 69.463 | 56.13 | 38.08 |
| 4 | 88.46 | 88.9 | 87.6 | 88.53 | 86.25 | 85.01 | 86.31 | 81.64 | 84.78 | 81.14 | 73.14 | 53.43 |
| 4 | | 86.64 | 86.52 | 87.27 | 84.89 | 87.3 | 84.22 | 85.48 | 80.75 | 79.39 | 73.43 | 59.19 |
| 4 | | | 87.25 | 89.26 | 87.17 | 87.45 | 85.29 | 83.88 | 80.74 | 81.08 | 72.94 | 61.02 |
| 4 ave | 88.46 | 87.77 | 87.123 | 88.35 | 86.1 | 86.59 | 85.27 | 83.67 | 82.09 | 80.537 | 73.17 | 57.88 |
| Total | 357.6 | 350.5 | 337.29 | 328.1 | 303.5 | 285.2 | 276.6 | 248.9 | 229.8 | 217.61 | 188.97 | 136.2 |
| Net 1–4 | 0 | 7.143 | 20.307 | 29.47 | 54.1 | 72.41 | 81.01 | 108.7 | 127.8 | 139.99 | 168.63 | 221.4 |
| MIU/ml | 1 | 50 | 100 | 200 | 400 | 800 | 1600 | 3200 | 6400 | 12800 | 25600 | 51200 |
| Log mIU/ml | 0 | 1.699 | 2 | 2.301 | 2.602 | 2.903 | 3.204 | 3.505 | 3,806 | 4.1072 | 4.4082 | 4.709 |

TABLE 7

| mIU/ml hCG | Ave Line 1–4 net Y | Calculated mIU/ml | % difference |
|---|---|---|---|
| 50 | 7.1 | 61.5 | 23 |
| 100 | 20.3 | 104 | 4.2 |
| 200 | 29.2 | 150 | 24.7 |
| 400 | 54.1 | 402 | 0.6 |
| 800 | 72.4 | 836 | 4.5 |
| 1600 | 81 | 1179 | 26.3 |
| 3200 | 108.7 | 3569 | 11.5 |
| 6400 | 127.8 | 7659 | 19.7 |
| 12800 | 140 | 12474 | 2.5 |

TABLE 8

| | Last line #1 | Last Line #2 | Last line #3 | Average |
|---|---|---|---|---|
| 50 | 1 | 1 | 1 | 1 |
| 100 | 1 | 1 | 1 | 1 |
| 200 | 1 | 2 | 1 | 1.3 |
| 400 | 2 | 2 | 2 | 2 |
| 800 | 3 | 2 | 2 | 2.3 |
| 1600 | 3 | 2 | 3 | 2.6 |
| 3200 | 4 | 3 | 3 | 3.6 |
| 6400 | 4 | 4 | 5 | 4.3 |
| 12800 | 6 | 5 | 5 | 5.3 |

TABLE 8-continued

| | Last line #1 | Last Line #2 | Last line #3 | Average |
|---|---|---|---|---|
| 25600 | 6 | 6 | 7 | 6.3 |
| 51200 | 7 | 7 | 7 | 7 |

Although the invention has been described with reference to the description and examples provided above, it should be understood that various modifications can be made without departing from the spirit of the invention.

We claim:

1. A conjugate having the formula

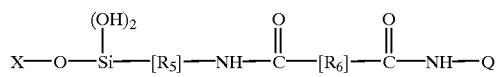

where X is a hydroxyl bearing solid phase material; $R_5$ is $(CH_2)_n(NH(CH_2)_m)_p$, where n is from 2 to 8, m is from 2 to 8, and p is from 0 to 3; $R_6$ is selected from the group consisting of alkyl, cyclic alkyl, aromatic and heterocyclic groups containing 0 to 8 hydroxyl, hydroxycarbonyl, or aminocarbonyl groups; and Q is any molecule that contains a free primary or secondary amine group.

2. The conjugate of claim 1 where X is selected from the group of nitrocellulose, cellulose, glass fibers and porous glass beads.

3. The conjugate of claim 2 where X is nitrocellulose.

4. The conjugate of claim 1 where R5 is a propyl group.

5. The conjugate of claim 1 where R6 is an alkyl group.

6. The conjugate of claim 5 where R6 is an ethyl group.

7. The conjugate of claim 1 where Q is selected from the group of molecules that intrinsically contain a free primary or secondary amine group and molecules to which a free primary or secondary amine group has been covalently attached.

8. The conjugate of claim 7 where Q intrinsically contains a free primary amine group.

9. A method for preparing the conjugate of claim 1, comprising:

applying Q in an aqueous solution to a chemically derivatized solid phase material having the formula

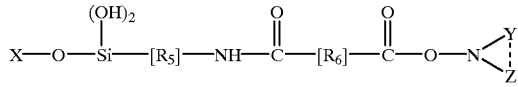

where X is a hydroxyl bearing solid phase material; R5 is (CH2)n(NH(CH2)m)p, where n is from 2 to 8, m is from 2 to 8, and p is from 0 to 3; R6 is selected from the group consisting of alkyl, cyclic alkyl, aromatic and heterocyclic groups containing 0 to 8 hydroxyl, hydroxycarbonyl, or aminocarbonyl groups; and Y and Z are independently hydrogen, alkyl alkyl carbonyl, aromatic carbonyl or heterocyclic carbonyl groups; or N, Y, Z together are succinimidyl, benzotriazolyl, or derivatives thereof;

drying the solid phase material;

washing the dried solid phase material; and redrying the washed solid phase material.

10. The method of claim 9 where X is selected from the group of nitrocellulose, cellulose, glass fibers and porous glass beads.

11. The method of claim 10 where X is nitrocellulose.

12. The method of claim 9 where R5 is a propyl group.

13. The method of claim 9 where R6 is an alkyl group.

14. The method of claim 13 where R6 is an ethyl group.

15. The method of claim 9 where N, Y and Z together are succinimide.

16. The method of claim 9 where N, Y, and Z together are N-hydroxybenzotriazole.

* * * * *